United States Patent [19]
Lindahl

[11] Patent Number: 6,083,518
[45] Date of Patent: *Jul. 4, 2000

[54] COMPOSITION COMPRISING AN ACTIVE AGENT DISSOLVED IN A GLASS-FORMING CARRIER AND A PROCESS FOR THE PREPARATION THEREOF

[75] Inventor: Åke Lindahl, Skurup, Sweden

[73] Assignee: Bioglan AB, Malmö, Sweden

[ * ] Notice: This patent issued on a continued prosecution application filed under 37 CFR 1.53(d), and is subject to the twenty year patent term provisions of 35 U.S.C. 154(a)(2).

[21] Appl. No.: 08/973,902

[22] PCT Filed: Jun. 19, 1996

[86] PCT No.: PCT/SE96/00806

§ 371 Date: Dec. 17, 1997

§ 102(e) Date: Dec. 17, 1997

[87] PCT Pub. No.: WO97/00670

PCT Pub. Date: Jan. 9, 1997

[30] Foreign Application Priority Data

Jun. 20, 1995 [SE] Sweden ................................. 9502244

[51] Int. Cl.7 .............................. A01N 25/04; A61K 9/10
[52] U.S. Cl. ......................... 424/405; 424/484; 424/485; 424/486; 424/487; 424/488; 523/218; 523/219
[58] Field of Search ..................... 523/218, 219; 428/404; 424/400–401, 405–484, 488

[56] References Cited

U.S. PATENT DOCUMENTS

| Re. 33,221 | 5/1990 | Brown et al. ........................... 423/308 |
| 4,151,273 | 4/1979 | Riegelman . |
| 4,938,964 | 7/1990 | Sakai et al. . |
| 5,470,880 | 11/1995 | Yu et al. ................................. 514/574 |
| 5,599,555 | 2/1997 | El-Nokaly ............................... 424/488 |

FOREIGN PATENT DOCUMENTS

| 0 543 541 A1 | 5/1993 | European Pat. Off. . |
| 0 552 708 A1 | 7/1993 | European Pat. Off. . |
| WO93/11749 | 6/1993 | WIPO . |

OTHER PUBLICATIONS

Chemical Abstract, vol. 110, 160316a, 1989.
Chemical Abstract, vol. 117, 118388V, 1992.
Chemical Abstract, vol. 109, 1988, 43367m.
Chemical Abstract, vol. 110. 1989, 121136x.
Chemical Abstract, vol. 117, 1992, 198406n.
Chemical Abstract, vol. 116, 1991, 158697f.
Chemical Abstract, vol. 115, 1991, 119925p.
Chemical Abstract, vol. 118, 240770z.
Chemical Abstract, vol. 115, 1991, 204011g.
Chemical Abstract, vol. 106, 1987, 143842u.
Chemical Abstract, vol. 116, 1992, 200985a.
Chemical Abstract, vol. 116, 1992, 113443d.
Chemical Abstract, vol. 117, 1992, 97163a.

*Primary Examiner*—Neil S. Levy
*Attorney, Agent, or Firm*—Burns, Doane, Swecker & Mathis, L.L.P.

[57] ABSTRACT

A biologically active composition comprising a solution of an active agent dissolved in a glass-forming carrier, which carrier comprises a glass-forming substance (A) containing a plasticizer (B), the amount of plasticizer preferably being selected so that the composition has a non-solid consistency. The composition can be prepared by dissolving the active agent in a melted mixture of the glass-forming substance and the plasticizer at a temperature below the decomposition temperature of said active agent. Use of the glass-forming carrier for dissolving a biologically active agent.

48 Claims, No Drawings

COMPOSITION COMPRISING AN ACTIVE AGENT DISSOLVED IN A GLASS-FORMING CARRIER AND A PROCESS FOR THE PREPARATION THEREOF

This application is a 371 of PCT/SE96/00806 filed Jun. 19, 1996 in Sweden and claims priority under 3545419e to application #9502244-8 filed in Sweden Jun. 20, 1995.

TECHNICAL FIELD

The present invention relates to the field of biologically active compositions and, in particular, to such a composition comprising a biologically active ingredient which, preferably, is a therapeutically active agent. However, other applications than within the medical field are also possible within the scope of the invention. More specifically the invention relates to a novel phase or formulation that is especially well adapted for formulating biologically active agents which are generally poorly water and fat soluble. Said novel formulation is potentially of great value because, by varying the composition thereof one can control the dissolution and/or release of the biologically active agent.

The invention also relates to said composition for use as a medicament as well as to a process for the preparation of said composition and to the use of a certain glass-forming carrier for a biologically active agent in a biologically active composition.

BACKGROUND OF THE INVENTION

In the development of novel medicines lately, great importance has been attached to creating as high uptake as possible of the active ingredient. Common to all medicines which are not administered by an injection is that they have to penetrate a biological membrane, e.g. the skin or the intestinal wall.

In the medical field the development of formulations for local or dermal applications has for many years primarily aimed at changing the properties of the skin so as to accomplish a more rapid penetration thereof. Research in the TDDS field, i.e. transdermal delivery systems, has led to the discovery of several so called enhancers. Such substances are utilized to change the properties of the skin so as to facilitate the penetration of the drug therein. However, skin properties are not the only parameters that dictate how rapidly the body will assimilate a locally administered drug. Several other factors are of a great importance, such as for instance the contact between skin and formulation, the extent to which local circulation is effected by the formulation and the solubility of the drug in the formulation. The problems are similar whether the preparations are administered locally or systemically.

Specific problems are encountered in connection with drug substances which are poorly soluble in conventional aqueous and fatty carriers. Thus, the bioavailability of a drug of this type is dictated by its dissolution rate which, in turn, is dependent on substances's particle size and specific surface area, or polymorph condition. Thus, it has been proposed to solve the problem associated with such drugs by reducing their particle size as much as possible. Other more or less complicated methods to be mentioned in this context are lyophilization, solvent deposition, solvate formation and the use of so called solid dispersions.

The technique of using solid dispersion is for instance disclosed in WO93/11749. The process disclosed therein, however, does not provide a satisfactory solution to the problems associated with poorly water and fat soluble drugs, and it does not enable any substantial variation of the dissolution or release rates of an active agent. The major reason for this drawback is that the active ingredient is still not in any substantially dissolved state. Furthermore, although a plasticizer is referred to therein, it is clearly disclosed that said plasticizer is used to facilitate the formation of a dispersion, the product manufactured being a solid powdery mass.

As prior art in connection with the invention reference can also be made to U.S. Pat. No. 4,151,273 and U.S. Pat. No. 4,938,964. U.S. Pat. No. 4,151,273 discloses the use of a glassy matrix as a carrier for a drug but said carrier is more or less non-variably solid and used in a powdered product, e.g. a tablet, for oral administration. Moreover, it does not suggest the use of any plasticizer. U.S. Pat. No. 4,938,964 discloses an adhesive carrier for ketoprofen, comprising a specific acrylic or methacrylic copolymer. Thus, also said carrier has a more or less fixed composition that does not enable any real compositional adjustments after the preparation thereof and is laminated on a solid film support. Furthermore, again, U.S. Pat. No. 4,938,964 does not include any reference to a plasticizer.

DESCRIPTION OF THE INVENTION

The present invention relates to a completely novel preparation or formulation for biologically active agents, and especially of the types referred to above, which may seem similar to the aforementioned solid dispersions, but which is of a completely different structure and thereby possessed of completely different properties as compared thereto. Although the ingredients used in the two cases are similar in their own right, the composition according to the present invention has been prepared in a completely different way to the previously known composition and, therefore, is of a completely novel structure and has different properties. More specifically, the composition according to the present invention is similar to a so called solid solution, i.e. the biologically active agent has been dissolved and not dispersed as in the prior art. By this novel measure it has been found possible to drastically increase or enhance the solubility or solubility rate of the active ingredient, in spite of the fact that the biologically active agent may be only sparingly soluble in water and fats.

In addition thereto the novel composition according to the invention differs essentially from the above-mentioned prior art disclosing the use of glassy carriers in that the physical characteristics as well as the release profile thereof, with reference to the active agent, can be controlled in an extremely simple and effective way merely by varying the composition thereof. As is readily understandable this gives a very versatile product as compared to the fixed carriers according to the prior art.

Thus, a first object of the invention is to provide a composition which is able to dissolve an active agent in spite of the fact that said compound is poorly or sparingly soluble in water and fats.

Another object of the invention is to provide a composition possessing an enhanced dissolution and/or release rate for the active agent.

Still another object of the invention is to provide a composition for use as a drug or medicinal.

One other object of the invention is to provide a composition, the consistency and release profile of which can be easily controlled by means of the composition thereof, i.e. the proportions between the ingredients present therein, especially to accomplish a composition to be administered via the skin.

Still another object of the invention is to provide a process for the preparation of a composition of the type referred to above.

Still other objects of the invention should be obvious to a person skilled in the art after having studied the following description of the invention.

Thus, it has now been found that a glass-forming carrier comprising a glass-forming substance and a plasticizer therefor can work excellently as a carrier for a biologically active agent in the formation of a biologically active composition showing outstanding characteristics.

More specifically the biologically active composition according to the present invention comprises a solution of a biologically active agent dissolved in a glass-forming carrier, which carrier comprises a glass-forming substance (A) containing a plasticizer (B).

That is, according to the invention it has been found that the new glass-forming carrier can dissolve a biologically active agent to a very great extent to the formation of a very versatile product provided specific considerations are made in connection with the glass-forming carrier and the preparation of the biologically active composition.

Thus, by means of the amount of plasticizer the consistency as well as activity characteristics of the composition can be controlled in a very simple way, contrary to the more or less fixed compositions in the prior art. According to a preferable embodiment of the invention this e.g. means that the composition comprises sufficient plasticizer to be non-solid at a temperature below the glass transition temperature (Tg) of the glass-forming substance alone.

Preferably the composition has a non-solid consistency at the intended use temperature of the composition and, optionally, at a temperature below 50° C., preferably below 40° C., more preferably within the range of –10° C. to 50° C. or –10° C. to 40° C., and most preferably within the range of 0° C. to 40° C.

The term non-solid should be interpreted in a broad sense and generally means liquid or jelly-like, where liquid typically means viscous, especially highly viscous, consistency.

According to another embodiment of the invention the glass transition temperature (Tg) of the carrier is chosen such that it allows for a dissolution of said biologically active agent at a temperature where significant decomposition of said agent is avoided.

According to yet another embodiment the glass transition temperature (Tg) of the solution is chosen such that it allows for a stable solution at use and/or storage.

According to still another embodiment of the invention the glass transition temperature (Tg) of the solution is chosen such that it allows for the manufacture of a stable solution without any significant decomposition of the biologically active agent.

In yet another embodiment of the invention significant thermally induced decomposition of the biologically active agent is avoided in a temperature range extending up to a temperature which exceeds the glass transition temperature (Tg) of the solution and/or carrier.

One of the great advantages of the invention is that it has been discovered that by proper choice of plasticizer and percentage thereof in the carrier or the composition not only the consistency of the composition can be adjusted to enable the utilization of the composition for many different applications and via many different administration methods, especially from a more or less viscous liquid, especially a highly viscous liquid, to a jelly like product, but also the release profile of the biologically active agent can be controlled to tailor the composition for a specific application. Moreover, this can be accomplished in an extremely simple way which means a great contribution to the existing technique with a rigid or fixed composition dictated by the method of manufacturing the carrier matrix.

Although different processes for the preparation of compositions according to the invention will be more specifically described below, it can thus be emphasized at this stage that the invention is based on the idea of utilizing a combination of glass-forming substance and a plasticizer as a carrier for the biologically active ingredient. In this context the term glass is used in the meaning of an amorphous single phase mass consisting of one or more ingredients which are dissolved in each other.

At room temperature, such substances can be below their so called glass transition temperatures (Tg), but dissolving a biologically active agent in a pure glass-forming substance often requires the materials to be heated to such a high temperature that the active agent will start decomposing. Moreover, a glass is not stable, i.e. it will eventually crystallize. However, when adding the plasticizer to said substance, its Tg is reduced, providing a reduction in viscosity which enables the addition and dissolution of the active ingredient at a lower temperature, i.e. in practice at a temperature where decomposition does not take place. According to the invention it has furthermore been found that by means of the plasticizer the dissolution rate/release rate, and the consistency, of the composition can be varied or controlled.

At the temperature at which it is preferably used, a composition according to the invention is similar to a solid solution, which is generally defined as an amorphous solid phase mass of two or more components dissolved in each other but, as it is above its glass transition temperature, it differs therefrom by typically being a more or less viscous, often highly viscous, liquid, or a jelly-like substance, rather than a solid. Such a solution can be a solid solution, in the form of a glass, below its Tg, but it is a non-glass above its Tg. The components of the composition are selected such that, however, one rarely passes below the glass temperature in normal use. In other words the invention can be considered to be a solid solution which is generally used and, preferably, stored at a temperature above its glass transition temperature Tg, where it is actually a more or less viscous liquid so as to avoid any risks of crystallization.

As was mentioned above this differentiates the invention from a solid dispersion, which consists of a particulate suspension of one or more substances in an amorphous mass. In such a case the active ingredient is not in a dissolved state but, by definition, the ingredient is present in a particulate state.

The biologically active agent is preferably a biologically active compound, and generally any such compound which can be dissolved into a solution in accordance with the present invention. However, the inventive composition is more likely to include an active compound which is poorly soluble in water and fats (or non-polar solvents), as it offers a solution to the special problems regarding the delivery of such substances. Preferably, the active compound has some hydrophilicity, in the sense that its molecular structure contains a large number of hydrophilic groups. As concerns the term "biologically active compound" said term should be interpreted in a broad, conventional sense to mean a compound which, when present in an effective amount, presents a therapeutic effect when exposed to living organisms.

Of course there are a large number of compounds falling within the above-mentioned definitions and which are then also utilizable according to the invention. However, some specific examples of interesting compounds are the antiviral compounds, especially guanoside compounds, such as acyclovir Vidarabin and Idoxuridin, and esters of antiviral substances, preferably fatty acid esters of antiviral guanoside derivatives; antimicrobial substances, such as e.g. erythromycin and metronidazol; antifungal compounds, e.g. griseofulvin and imidazoles; corticosteroids; vitamins; provitamins; hormones such as e.g. estradiol; antiinflammatory compounds, such as e.g. piroxicam, Indomethacin, clotrimazol or salicylic acid or derivatives thereof, e.g. acetylsalicylic acid and 4-5-aminosalicylic acid; flavonoids, such as e.g. Catechin, etc; anticancer agents, especially folic acid antagonists, e.g. metotrexate; and psychopharmaceutical drugs, e.g. Busulphan.

Generally these compounds have low water solubilities and in some instances, such as the guanoside compounds, can have polar properties in spite of said low water solubility. In this connection it should be noted that the term low water solubility, or similar, can not and need not be limited to specific figures, due to the nature of the invention. However, it can be added that such a compound as ketoprofen or similar may be excluded from the scope of protection according to one embodiment of the invention.

The glass-forming substance is generally selected from conventional substances having the ability to form a glass or, more specifically, a solid solution of the type defined above. Specific consideration should be given to the fact that melting temperature, glass transition temperature (Tg) and viscosity should suit the selected biologically active compound and the use envisaged for the composition after the addition of the plasticizer. In other words a number of glass-forming substances would work according to the invention provided that the Tg requirements are fulfilled, which generally means a Tg above 0° C. Some general types of glass-forming substances are mono and oligosaccharides and polymers, e.g. polyvinylpyrrolidone, fulfilling the above-mentioned requirements. Polyalkylene glycols, such as polyethylene glycol, are other examples of useful substances and an especially preferable glass-forming substance is citric acid, as it is of a non-complex nature.

It should hardly need mentioning that the glass-forming substance as well as the plasticizer and other optional further ingredients should also be pharmaceutically acceptable and non-toxic in the compositions' intended use.

The plasticizer is also chosen in line with known principles, i.e. a substance is selected which has the ability of working as a plasticizing agent for the selected glass-forming substance, the ability to form a solid solution in combination therewith and the ability to provide the composition with the required glass temperature. Some examples of suitable plasticizers include alcohols, viz. mono-, di-, tri- and ternary alcohols, especially alcohols comprising at least two —OH groups, as well as other polar solvents, such as carbonates, and low molecular weight polymers. Also organic acids can be used. Specific examples of alcohols are glycerol, propylene glycol and dipropylene glycol. Last-mentioned two alcohols could also be referred to as examples of said polymers. A preferred carbonate is propylene carbonate, while a preferred example of an organic acid is lactic acid.

It should also be added that the invention is not limited to the use of added, so called external plasticizers although this represents the preferred embodiment of the invention. Thus, the principles of the invention should be usable also in connection with internal plasticizers chemically reacted with the glass-forming substance to plasticize the same.

As has been mentioned, in preferred embodiments, the inventive composition is a medical or pharmaceutical composition. In such a case the composition can of course contain additives of those types which are conventionally used in pharmaceutical compositions. Specifically, since the composition when used as a medicinal is primarily intended for administration via the skin, a skin penetration-enhancing substance can be included therein. The main purpose of using such a substance is to change the properties of the skin or to improve the contact with the skin. Examples of suitable substances of this kind are oleic acid, oleyl alcohol, monoolein and/or salicylic acid. Also mono, di or triglycerides can be added to products for oral use for the purpose of utilizing the fat-absorption mechanisms of the body itself to increase the uptake of drug from the intestines. Thus, the composition can be used also for other administration routes than by dermal administration, such as for oral, buccal, vaginal, rectal, intranasal or intravaginal administration, provided provisions can be taken to adapt the liquid or gel consistency to such administrations. Other additives may be introduced into the composition for the purpose of altering the pH, osmolarity and other general properties of the composition in contact with biological fluids or for dissolution purposes. Preservatives may also be added to the composition in order to increase microbiological stability.

The combination of glass-forming substance and the plasticizer therefor should be selected in line with the principles given above such that proper glass transition temperature, consistency, release profile, etc. are obtained. Typically this means that the percentage of glass-forming substance is in the range of 10–90% by weight, preferably 20–80% by weight and that the percentage of plasticizer is in the range of 90–10% by weight, preferably 80–20% by weight, based on the combined weight of the glass-forming substance plus the plasticizer. A more preferable percentage of the glass-forming substance is in the range of 30–70% by weight and a more preferable percentage of the plasticizer is in the range of 70–30% by weight, expressed on the same basis.

In preferred embodiments, the glass transition temperature Tg of the glass-forming carrier or of the solution is below 0° C., preferably below –10° C. Furthermore, in many cases it may be preferable to choose the composition in such a way that Tg will be below –20° C. and even more preferred below –30° C., to thereby reduce the rate of crystallization of the glass and such that a substantially stable product is accomplished. Thus, the quantity of plasticizer is selected to provide the required glass transition temperature to the composition.

The amount of the biologically active agent is of course dependent on the effect to be accomplished, which means that such amount cannot easily be expressed in specific numbers. Generally, however, the upper limit will be the solubility limit in the inventive solution, which can be up to 10% by weight or in some cases merely up to 5%, in both cases calculated on the weight of the glass-forming carrier. Preferably the range thereof can be 0.01–10, especially 1–10, or 0.01–5, especially 1–5, percent by weight, on the same basis. In specific cases the amount thereof is preferably less than 5%, somtimes less than 2%, by weight of the active agent, based on the weight of the glass-forming carrier. The exact amount, however, is easily determined by a person skilled in the art with reference to the optimum or maximum effect it is wished to obtain.

Of the additives referred to above, the inclusion of a skin penetration-enhancing substance is especially preferred. Again the nature and amount of such a substance is easily chosen by a person skilled in the art so as to obtain a maximum or optimum effect. Typically said substance or any other additive is utilized in the range of 0–10% by weight, based on the total weight of the glass-forming carrier.

An especially preferred use of the composition according to the invention is, as was mentioned above, as a pharmaceutical composition. In this case the biologically active agent is of course a therapeutic or prophylactic compound of any kind. The other ingredients of the composition are selected in accordance with the general principles for pharmaceutical compositions. However, the composition is of course utilizable in all applications where it is desired to solubilize agents, especially such agents which are poorly water or fat soluble per se.

In an especially preferred embodiment the inventive composition comprises a medicament for administration to the skin, or for dermal administration. In such a case a person skilled in the art will formulate the composition such that its viscosity will be proper for administration in that way and so that the release of the active compound will have the desired profile. By varying the composition in this way one can, thus, easily and effectively control the release both as regards the time profile and the amount profile, to achieve a controlled or sustained release, which of course also applies to other administrations than dermal administration.

According to another embodiment of the invention the composition claimed is adapted for an oral or buccal administration thereof. The composition is then preferably prepared in such a way that the viscosity of the preparation allows for a filling in hard or soft gelatine capsules. In this way the release of the active ingredient from the preparation can be enhanced and prerequisites for a higher bioavailability are created.

According to still another embodiment of the invention the composition is adapted for vaginal or rectal administration thereof. In such a case the composition is preferably prepared in such a way that the viscosity thereof makes the product ready for such an administration as it is. Aternatively, however, the final product can comprise a product containing droplets of the composition dispersed in a waxy, fatty or polymeric mass having a proper melting point for this specific type of administration, which is generally around 35° C. (a so called suppository mass).

Another embodiment of the invention is represented by a composition adapted for an intranasal or intravaginal administration thereof. Then the product is preferably prepared as a foam and in such a way that droplets of the preparation are homogeneously distributed on the application surfaces.

According to another aspect of the invention there is provided a process for the preparation of the biologically active composition which can be as defined above. Said process comprises melting the glass-forming carrier, preferably to form an amorphous single phase mass, and dissolving a biologically active agent in the molten carrier at a sufficiently low temperature to prevent significant decomposition of the biologically active agent.

As was mentioned above the glass forming carrier comprises a glass-forming substance (A) and a plasticizer (B), and a mixture of the glass-forming substance (A) and the plasticizer (B) is melted to form the single phase mass. Optionally, a skin penetration-enhancing substance (C) or any other additive can be dissolved in the single phase mass.

In a preferred embodiment, the glass-forming substance is heated to a temperature above its melting point and the plasticizer is added to the melted mass, or the glass-forming substance is heated together with the plasticizer to form an amorphous single phase mass in the melted state. Typically, the temperature to which the mixture of the glass-forming substance with the plasticizer, prior to dissolution, is heated, is too high to enable the direct addition of the biologically active agent without causing it to decompose. Preferably, therefore, the melted mass is firstly cooled to a temperature at which the active agent can still be added and dissolved. The presence of the plasticizer reduces the viscosity and thereby a rapid dissolution of the active agent can be obtained at a lower temperature than if a pure glass-forming substance were utilized.

The resulting solution, which includes the biologically active agent dissolved in the amorphous mass, is then preferably cooled down to the desired storage or use temperature. Said storage or use temperature is, as was mentioned above, still above, and preferably substantially above, the glass transition temperature of the composition, as the risk of causing crystallization, thus, is thereby avoided or essentially eliminated. Compositions prepared by the inventive process, therefore, possess a high stability.

As should be clear from the description above one of the advantages of the invention is that it does not involve the use of water and/or any volatile organic solvent in the manufacturing process. Consequently the composition claimed is substantially free of water and/or volatile organic solvent.

Generally the temperature at which the composition is stable for use is between −10° C. and 50° C., preferably above 10° C. and, more preferably, the body temperature of a human or animal recipient. These temperatures also generally represent the "intended use temperature" of the composition, although such temperature can not be specifically given in exact figures due to the general applicability of the composition according to the invention. However, for a person skilled in the art "use temperature" should be a definite term as it should be known or easily estimated in each specific case.

The temperature at which the composition is stable for storage often lies between −10° C. and 30° C., preferably between 5° C. and 20° C.

According to one embodiment of the process according to the invention the biologically active agent is dissolved as such directly in the melted mass. Preferably this is the case when the biologically active agent exists in a powder form.

In another embodiment, the biologically active agent is firstly dissolved or suspended in a portion of the plasticizer and the resulting solution or suspension is then added to the melted amorphous mass.

One interesting type of formulation of the composition claimed is in the form of drops. An example of the preparation of such a formulation is the homogenization operation set out in Example 4 below, which provides an emulsified "solid" solution in a continuous petrolatum phase.

The specific temperatures used for the initial melting of the glass-forming carrier, or during the dissolution of the biologically active agent in the melted product, respectively, are of course easily determined by a person skilled in the art in each specific case and general instructions in this respect are not easily given. Typically, however, the initial melting operation is performed at a temperature in the range of 90–170° C., preferably 105–160° C., and the molten carrier is then cooled down to a temperature in the range of 60–120° C., preferably 80–110° C., before the biologically active agent is dissolved therein.

Finally, still another aspect of the invention is the use of the glass-forming carrier as defined above for dissolving a biologically active agent in the formation of a biologically active composition.

Preferable embodiments of said use are similar to the preferable embodiments described above in connection with the composition or process and need not be repeated once more.

EXAMPLES

The invention will now be exemplified further by means of the following non-limiting working examples, wherein the commercial preparation referred to was Zovirax cream (a cream containing 5% of acyclovir).

Example 1

4 g of citric acid and 4 g of glycerol were heated to 160° C. and admixed to a homogenous mass. Said mixture was allowed to cool down to 80° C. In the meantime 0.5 g of acyclovir was stirred into glycerol heated to 80° C. to form a suspension of acyclovir in glycerol. Said suspension was in turn stirred into the first melt of citric acid and glycerol, the temperature still being 80° C. The stirring operation was continued until the suspension became clear, whereupon the solution obtained was cooled down to room temperature. Thus, firstly this experiment shows that it is possible to dissolve 5% by weight of acyclovir into a viscous liquid "solid" solution in accordance with the invention.

The preparation obtained showed a dissolution rate in a Franz-cell which was 50 times higher than that of a commercial preparation of acyclovir.

Franz-cells are disclosed in an article by Franz, T. J., Percutaneous absorbance. On the relevance of . . . , J. Invest., Dermatol 67, 190, 1975. Penetration experiments in a Franz-cell is an in vitro method for the determination of the penetration rate of a drug through a polymeric membrane or through a skin cut.

Example 2

4 g of citric acid was melted together with 5.5 g of propylene glycol at 110° C. under stirring. When the citric acid had been dissolved, the temperature was lowered to +80° C. and 0.5 g of acyclovir was added. After a few minutes, when the acyclovir had been dissolved, the temperature was lowered to room temperature.

In tests performed on humans it was found that the amount of acyclovir in urine after 24 h of dermal application of said product was approximately 10 times higher than after application of a commercial product.

Example 3

5.1 g of citric acid was mixed with 4.1 g of propylene glycol at 105° C. At the same temperature 0.5 g of acyclovir, 0.19 g of oleyl alcohol and 0.14 g of Brij 98 were admixed. The two products were then mixed with each other, the temperature still being 105° C. The resulting formulation was then allowed to cool down to room temperature.

In penetration experiments on healthy human volunteers said formulation showed substantially higher amounts of acyclovir in the urine, viz. 5–10 time higher, than when using the corresponding commercial acyclovir preparation.

Example 4

4 g of citric acid was mixed at 80° C. with 4 g of propylene glycol. In the meantime 0.5 g of acyclovir was admixed with 1.5 g of propylene glycol at the same temperature. The two products were then mixed with each other, the temperature still being maintained at 80° C.

20 g of white petrolatum was heated to 60° C., whereupon the solution of acyclovir in citric acid and propylene glycol was added to the petrolatum. The internal phase, comprising the solution of acyclovir in citric acid and propylene glycol, was homogenized to a proper drop size and the temperature of the resulting formulation was reduced down to 25° C. with continued stirring.

Example 5

5.9 g of citric acid and 3.7 g of propylene glycol were heated to 110° C. and admixed to a homogeneous mass. When said mixture was clear, 0.2 g of oleoyl alcohol and Brij 98 were added and when a clear solution was obtained said solution was cooled to 100° C.

0.12 g of griseofulvin was then added and after a clear solution had been obtained this was cooled to room temperature to provide a viscous liquid solution containing 1.2% of griseofulvin.

| EXAMPLE 6 | |
| --- | --- |
| Acyclovir | 0.75 g |
| Citric acid | 4.0 g |
| Polyethylene glycol | 5.5 g |

The preparation is made in accordance with Example 2 and after cooling to room temperature the viscous product is filled onto hard gelatine capsules.

| EXAMPLE 7 | |
| --- | --- |
| Metronidazol | 1 g |
| Citric acid | 8 g |
| Polyethylene glycol | 2 g |

The preparation from Example 2 is repeated and while still having a temperature of 40–50° C. the mass is filled onto suppository moulds. After cooling to room temperature the suppositories are packed in suitable packages, e.g. aluminium/plastic folio in two layers.

| EXAMPLE 8 | |
| --- | --- |
| Metronidazol | 7% (by weight) |
| Citric acid | 40% |
| Propylene glycol | 26% |
| Glycerol | 26% |
| Foaming agent | 0.25% |
| Foam stabilizer | 0.75% |

The preparation is made in accordance with Example 7 with the exception that the two plasticizers are admixed before the addition. The foaming agent and the foam stabilizer are added before cooling to room temperature.

Example 9

Citric acid 4 g and glycerol 4 g were mixed and heated to 160° C. The mixture was allowed to cool to 80° C. and triethanolamine 2 g were mixed into the structure. When the mixture was clear, i.e. everything in solution, 0.5 g of acyclovir was added and allowed to dissolve completely prior to cooling to room temperature.

What is claimed is:

1. An amorphous single phase biologically active liquid or gel composition consisting of a biologically active agent dissolved in a glass-forming carrier;
   wherein said glass-forming carrier consists of a glass-forming substance selected from the group consisting of citric acid, monosaccharides, oligosaccharides, polyalkylene glycols and polyvinylpyrrolidone in the range of 10–90 percent by weight and a plasticizer in the range of 90–10 percent by weight, based on the combined weight of glass-forming substance and plasticizer; and
   wherein the biologically active agent is selected from the group consisting of antiviral compounds, antimicrobial compounds, antifungal compounds, corticosteroids, vitamins, provitamins, hormones, antiinflammatory compounds, anticancer agents and psychopharmaceutical compounds.

2. The composition of claim 1, wherein the biologically active agent is a biologically active compound which is water and fat insoluble.

3. The composition of claim 1, wherein said active agent is a guanoside compound or a fatty acid ester thereof.

4. The composition of claim 1, wherein said active agent is selected from the group consisting of erythromycin, metronidazole, griseofulvin and imidazoles.

5. The composition of claim 1, wherein said active agent is estradiol.

6. The composition of claim 1, wherein said active agent is selected from the group consisting of piroxicam, indomethacin and clotrimazol.

7. The composition of claim 1, wherein said active agent is a salicylic acid, acetylsalicylic acid, 4-aminosalicylic acid or 5-aminosalicylic acid.

8. The composition of claim 1, wherein said active agent is a flavonoid.

9. The composition of claim 1, wherein said active agent is a folic acid antagonist.

10. The composition of claim 1, wherein said active agent is busulphan.

11. The composition of claim 1, wherein said plasticizer is selected from the group consisting of alcohols, carbonates, low molecular weight polymers and organic acids.

12. The composition of claim 11, wherein said plasticizer is selected from the group consisting of glycerol, propylene glycol, dipropylene glycol, propylene carbonate and lactic acid.

13. The composition of claim 1, further comprising a skin penetration-enhancing substance.

14. The composition of claim 13, wherein said skin penetration-enhancing substance is selected from the group consisting of oleic acid, oleyl alcohol, monoolein and salicylic acid.

15. The composition of claim 1, further comprising a mono, di, or tri-glyceride as a fat-absorption enhancing substance to increase the uptake of the biologically active agent from the intestines.

16. The composition of claim 1, wherein the amount of the biologically active agent is up to the solubility limit thereof.

17. The composition of claim 1, wherein said biologically active agent is present in an amount of up to 10% by weight, based on the weight of the glass-forming carrier.

18. The composition of claim 1, wherein the amount of the skin penetration-enhancing substance is present in an amount of up to 10% by weight, based on the weight of the carrier.

19. A medicament comprising the biologically active composition of claim 1, said biologically active agent being a therapeutically or prophylactically active agent.

20. The medicament of claim 19, wherein said medicament is useful for dermal application.

21. A process for the preparation of an amorphous single phase biologically active liquid or gel composition consisting of melting a glass-forming carrier and dissolving a biologically active agent in the molten carrier;
   wherein said glass-forming carrier consists of a glass-forming substance selected from the group consisting of citric acid, monosaccharides, oligosaccharides, polyalkylene glycols and polyvinylpyrrolidone in the range of 10–90 percent by weight and a plasticizer in the range of 90 to 10 percent by weight, based on the combined weight of glass-forming substance and plasticizer; and
   wherein the biologically active agent is selected from the group consisting of antiviral compounds, antimicrobial compounds, antifungal compounds, corticosteroids, vitamins, provitamins, hormones, antiinflammatory compounds, anticancer agents and psychopharmaceutical compounds.

22. The process of claim 21, wherein the molten carrier is cooled to below the decomposition temperature of the active agent before said active agent is dissolved therein.

23. The process of claim 21, wherein the biologically active agent is dissolved in the molten carrier by adding the biologically active agent in powdered form directly to said molten carrier.

24. The process of claim 21, wherein the biologically active agent is dissolved in the molten carrier by dissolving or suspending the biologically active agent in a part of the plasticizer and then adding the solution or suspension obtained thereby to said molten carrier.

25. The process of claim 21, wherein the initial melting operation is performed at a temperature in the range of 90–170° C. and the molten carrier is then cooled down to a temperature in the range of 60–120° C. before dissolving the biologically active agent therein.

26. The process of claim 21, further comprising the step of cooling the composition down to a storage temperature.

27. The process of claim 26, wherein the storage temperature is above the glass transition temperature (Tg) of the composition.

28. The composition of claim 1, wherein the temperature at which the composition is stable for storage is between −10 and +30° C.

29. The composition of claim 1, wherein said composition is a liquid.

30. The composition of claim 1, wherein said composition is a gel.

31. The composition of claim 1, wherein the temperature at which the composition is stable for storage is between 5 and 20° C.

32. The composition of claim 3, wherein said active agent is selected from the group consisting of acyclovir, vidarabin and idoxuridin.

33. The composition of claim 7, wherein said active agent is selected from the group consisting of acetylsalicylic acid and aminosalicylic acid.

34. The composition of claim 7, wherein said active agent is 4,5-aminosalicylic acid.

35. The composition of claim 8, wherein said active agent is catechin.

36. The composition of claim 9, wherein said active agent is methotrexate.

37. The composition of claim 1, wherein said glass-forming substance has a Tg above 0° C.

38. The composition of claim 1, wherein the amount of glass-forming substance is present in the range of 20–80 percent by weight and the amount of plasticizer is present in the range of 80–20 percent by weight.

39. The composition of claim 1, wherein the amount of glass-forming substance is present in the range of 30–70 percent by weight and the amount of plasticizer is present in the range of 70–30 percent by weight.

40. The composition of claim 17, wherein said biologically active agent is present in an amount of 0.01–10% by weight, based on the weight of the glass-forming carrier.

41. The composition of claim 17, wherein said biologically active agent is present in an amount of 1–10% by weight, based on the weight of the glass-forming carrier.

42. The composition of claim 20, wherein said mammal is a human.

43. The process of claim 25, wherein the initial melting operation is performed at a temperature in the range of 105–160° C. before dissolving the biologically active agent therein.

44. The process of claim 21, comprising the further step of cooling the composition.

45. The process of claim 26, wherein the storage temperature is between −10 and +30° C.

46. The process of claim 26, wherein the storage temperature is between 5 and 20° C.

47. The process of claim 21, wherein said composition is a liquid.

48. The process of claim 21, wherein said composition is a gel.

* * * * *